(12) United States Patent
Beden et al.

(10) Patent No.: US 7,503,915 B2
(45) Date of Patent: Mar. 17, 2009

(54) DEVICE FOR THE TREATMENT OF A MEDICAL FLUID

(75) Inventors: Josef Beden, Mainz-Kastel (DE); Martin Herklotz, Heusenstamm (DE); Joerg Scherer, Bad Homburg (DE); Hans-Peter Schneider, Neu Anspach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 628 days.

(21) Appl. No.: 10/303,698

(22) Filed: Nov. 26, 2002

(65) Prior Publication Data

US 2003/0100882 A1    May 29, 2003

(30) Foreign Application Priority Data

Nov. 26, 2001 (DE) .................................. 101 57 924

(51) Int. Cl.
*A61K 9/22* (2006.01)

(52) U.S. Cl. ..................................................... 604/890.1

(58) Field of Classification Search ................. 604/403, 604/151, 29, 30, 890.1; 417/16, 395; 210/258, 210/218, 646

See application file for complete search history.

(56) References Cited

U.S. PATENT DOCUMENTS

| 5,062,774 | A | * | 11/1991 | Kramer et al. | ........... | 417/413.1 |
| 5,378,126 | A | * | 1/1995 | Abrahamson et al. | ....... | 417/479 |
| 5,628,908 | A | | 5/1997 | Kamen et al. | | |
| 5,738,662 | A | | 4/1998 | Shannon et al. | ............. | 604/247 |
| 5,938,634 | A | | 8/1999 | Packard | ....................... | 604/29 |
| 5,989,423 | A | * | 11/1999 | Kamen et al. | ................ | 210/258 |
| 7,041,076 | B1 | * | 5/2006 | Westberg et al. | ........... | 604/6.01 |

FOREIGN PATENT DOCUMENTS

| DE | 195 48 537 | 7/1996 |
| DE | 196 22 050 | 12/1997 |
| DE | 198 37 667 | 3/2000 |
| JP | 3113886 | 12/2000 |
| WO | 01/17606 | 3/2001 |

* cited by examiner

*Primary Examiner*—Nicholas D Lucchesi
*Assistant Examiner*—Christopher D Koharski
(74) *Attorney, Agent, or Firm*—Jacobson Holman PLLC

(57) ABSTRACT

A device for the treatment of a medical fluid including a permanently installed fluid treatment machine and a cassette with fluid-carrying channels as well as an elastic matt placed between these two items. The matt channels are recessed in the elastic matt and are provided with slits. Via the matt channels, an optimised vacuum distribution takes place and the slits serve the purpose of removing air between the cassette and the fluid treatment machine.

27 Claims, 2 Drawing Sheets

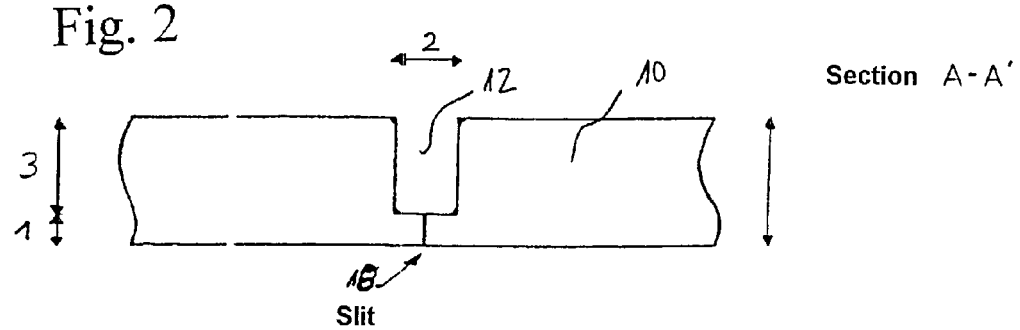
Fig. 2 Section A-A'
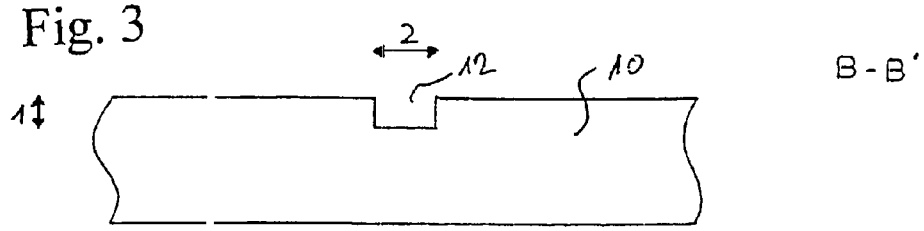
Fig. 3 B-B'
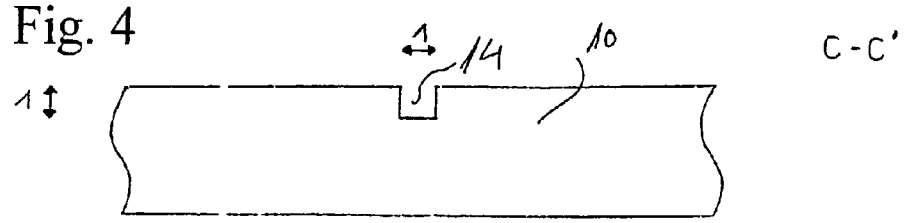
Fig. 4 C-C'

DEVICE FOR THE TREATMENT OF A MEDICAL FLUID

BACKGROUND OF THE INVENTION

1. Field of the Invention

The invention relates to a device for the treatment of a medical fluid including a permanently installed fluid treatment machine, a cassette with fluid carrying channels and an elastic matt placed between the fluid treatment machine and the fluid-carrying channels.

2. Description of the Related Art

Such devices are generally known and consist of a permanently installed fluid treatment machine, a cassette with fluid carrying channels which are sealed with a foil, and an elastic matt placed between these two items. Medical fluids to be treated can be blood, for example, but also dialysis fluids for the peritoneal as well as the haemodialysis. The relevant cassettes are advantageously formed as disposable units. Such a fluid treatment machine can also be a device for measuring of parameters of medical fluids, for example, as described in the DE 198 37 667 A1.

In these devices, a low pressure is created between the elastic matt and the cassette in order to prevent a deformation of the foil during low pressure in the channel, which leads to a channel restriction in the cassette, in order to be able to lift the foil at the adding points for the medical fluid and thus keep the access free, in order to prevent an air compliance in the pumping device and in order to be able to guarantee at special sensor positions an air-free attachment between the sensor surface and the foil.

The extraction of air requires openings on the machine and an extraction unit connected to them, a vacuum pump for example, whereby the distribution of the vacuum should be guaranteed to be as evenly as possible and positive across the entire foil surface of the cassette.

SUMMARY OF THE INVENTION

It is the object of the present invention to further develop the generic device such that, during operation, a problem-free air extraction is made possible whereby in this case the vacuum should be evenly distributed across the surface of the elastic matt and a simple and problem-free air extraction should be possible while, during the machine's idle time, the openings necessary for the air extraction should at least be largely closed.

In terms of the invention, this object is solved by a device for the treatment of a medical fluid including a permanently installed fluid treatment machine, a cassette with fluid carrying channels and an elastic matt placed between the fluid treatment machine and the fluid-carrying channels. The matt channels are recessed in the elastic matt, with the path of said channels following the fluid-carrying channels of the cassette. Starting from a vacuum connection of the elastic matt to the extraction unit, the matt channels reach all important points of the elastic matt. In order to avoid leaks when applying pressure to the channel beads of the top-mounted cassette, these matt channels lie within the channel structure of the cassette. Only where, within the cassette, too, there is a channel or another fluid-carrying structure as part of the cassette, there is also a corresponding matt channel in the elastic matt. In the matt channels, slits have been placed. These slits provided in the elastic matt behave in a similar manner as a lip seal. As a result of applying a vacuum, air can be extracted from between the fluid treatment machine and the cassette because the perimeter areas of the slits are pulled in due to the vacuum and its connection to an opening. However, due to the return force of the elastic material, these slits close immediately once the vacuum connection is interrupted, i.e. when the device is in an idle state or when there is no significant differential pressure. In this state, an ingress of fluid is securely prevented. On the other hand, when the slits are open, the access to the extraction unit, i.e. the continuation from the matt to the vacuum pump, can be protected against unintended ingress of fluid by suitable measures (e.g. filter).

According to a preferred embodiment, along the matt channels, the slits can be interrupted repeatedly for short intervals. That way, the slits are afforded a sufficient stability which enhances their valve function.

At certain points, a continuation of the vacuum line is not possible via the matt channels that run within the cassette channels because there are, for example, recesses provided in the elastic matt, which interrupt the matt channels. These recesses engage, for example, with pump membranes or valves on the machine. This structure would lead to a situation where a trouble-free air extraction via the matt channels can no longer take place. In order to nevertheless provide a full surface contact between the cassette and the machine, with said contact being as leak-proof as possible, and in order to extend the required vacuum source efficiently to the various areas of the contact surface, additional flatter connection channels compared to the matt channels are formed here, which by-pass the large-area recesses within the elastic matt. The execution of these connection channels is so shallow and so narrow that the nearby matt material of the elastic matt retains sufficient self-stability in order to prevent a deformation and closing of the connection channel even during the application of the vacuum and the distortion. Due to this preferred design, it is guaranteed that the slits and channels during distortion and application of the vacuum remain open and the matt remains sufficiently stable while the sealing effect of the matt remains intact and the channel structure provided is sufficient for the air flow to be extracted.

Finally, in the preferred arrangement, the elastic matt is designed to be exchangeable.

BRIEF DESCRIPTION OF THE DRAWINGS

Further details and advantages of the invention are explained more closely by way of an embodiment shown in the drawing. Shown are:

FIG. 2: a section along the section line A-A',
FIG. 3: a section along the section line B-B',
and
FIG. 4: a section along the section line C-C'.

DETAILED DESCRIPTION OF THE PREFERRED EMBODIMENTS

Figure 1:
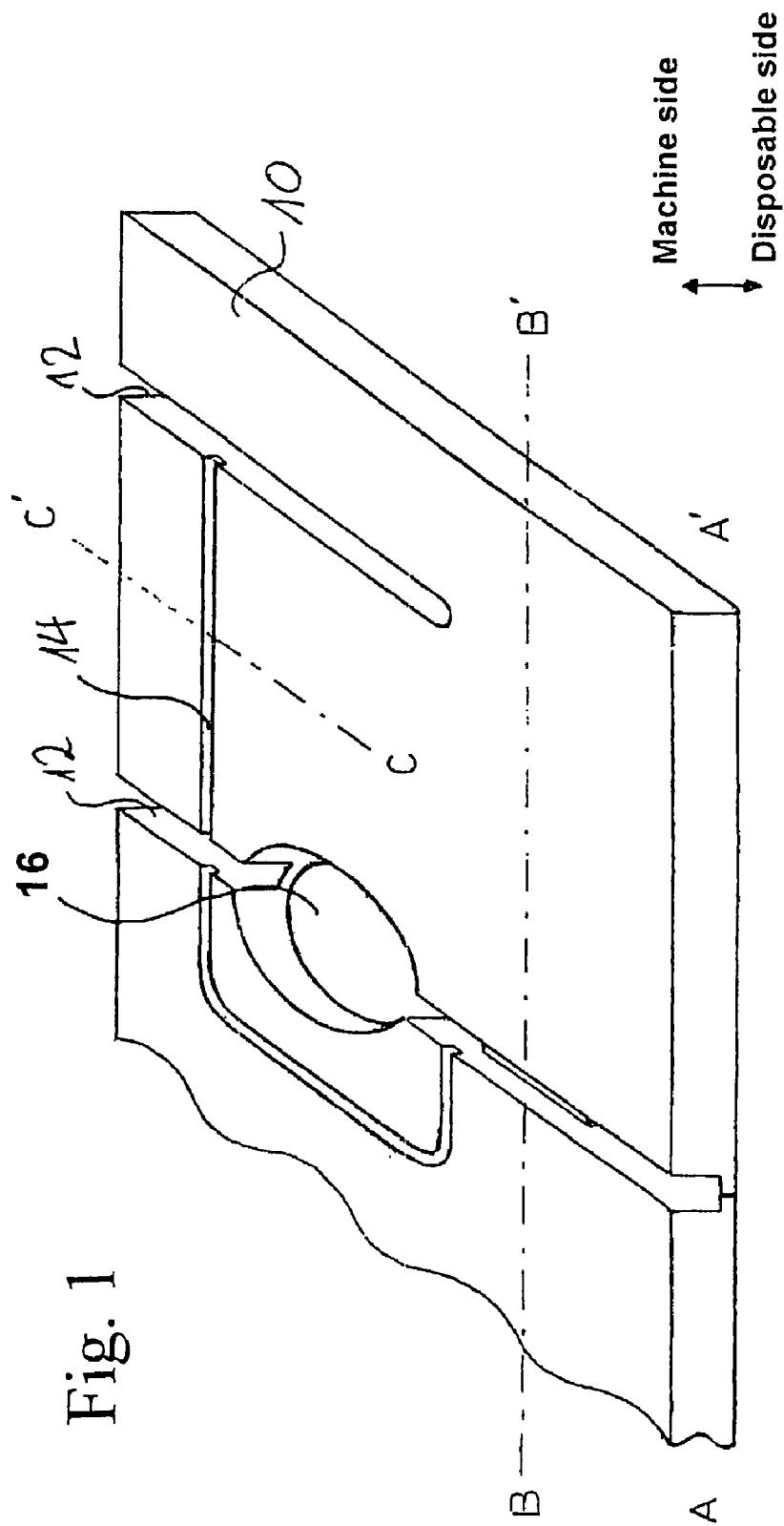
FIG. 1: a schematic, 3D representation of a section of an elastic matt according to an embodiment of the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In FIG. 1, an elastic matt 10 is shown schematically which is arranged between a fluid treatment machine, of which no detail is shown here, and a cassette (disposable) which is usually formed as a disposable unit. On the so-called machine side, namely on the surface which, when assembled, faces the fluid treatment machine, matt channels 12 and connection channels 14 are formed. Furthermore, a recess 16 is arranged in the elastic matt 10, into which in the assembled condition a machine-mounted valve, for example, engages and establishes a seal all around. It is easy to see that this machine-mounted valve interrupts the respective matt channel 12 which happens to join the recess 16. In order to still make an air extraction possible, a connection channel 14 has been provided which connects the two interrupted branches of matt channel 12 and connects them in turn with a further, parallel matt channel 12. The structure shown here is, of course, only an example and can be changed in any way. While the channel structures are provided on the machine side of the elastic matt 10, the disposable side, namely the side facing the cassette, is executed as a smooth, i.e. flat surface.

By referring to the sectional views of FIGS. 2 to 4, the structure of the individual channels can be explained in more detail. The section A-A' as per FIG. 1 is shown in FIG. 2 where a matt channel becomes visible which, with the elastic matt used here having a thickness of 4 mm, has a depth of 3 mm and a width of 2 mm. In the remaining matt material below channel 12, which has a thickness of 1 mm, a slit 18 is placed which takes on a type of valve function. When a vacuum is applied, the two areas of the elastic matt 10 adjacent to the slit 18 will open and enable the extraction of air gas. In an idle state or when an equilibrium is obtained, the two adjacent areas return to their original position and close the opening. In order to enhance this return effect, areas between the slits 18 are provided in the matt channel 12, which on the one hand do not have a slit and, on the other hand, are less deeply recessed in the area of matt channel 12. A corresponding area can be seen in section B-B' as per FIG. 3 which shows that, while the matt channel 12 in this area has the same width of 2 mm, it only has a depth of 1 mm.

In the view as per FIG. 4, a connection channel 14 is shown in the sectional view of C-C', where said channel is narrower and not as deep as the matt channel 12, which can be seen clearly in this view. In this case, both the width of the connection channel 14 and the depth are one millimetre each.

With the elastic matt according to this invention, it is guaranteed that the interior space of the fluid treatment machine, in its idle state, is protected by the self-closing feature of slits 18. At the same time, an even air extraction is achieved between the fluid treatment machine and the cassette across its entire surface because parallel extraction takes place via numerous slits 18. Thus, a minor blockage may not cause any detrimental effects for other areas.

With a thin matt 10, as it has been presented in the embodiment for example, the opening effect of the slits can be utilised by applying a vacuum.

Since the elastic matt 10 is exchangeable, it can be replaced easily after contamination or a fault. It is especially advantageous that no structured shapes are required for the fixed components on the machine. On the side of the elastic matt 10 facing the machine, open structures can be formed so that no sub-surface tunnels or other closed structures are required. On the other hand, the side of the elastic matt 10 facing the cassette is largely formed as a smooth, closed surface which can be cleaned easily for example.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A device for the treatment of a medical fluid, said device comprising a permanently installed fluid treatment machine, a cassette with fluid carrying channels and an elastic matt placed between the fluid treatment machine and the cassette, said elastic matt extending over substantially an entire face of said cassette and protecting an interior space of the fluid treatment machine, said matt having a substantially uniform thickness across said face into which channels are recessed, with paths of said matt channels respectively corresponding with paths of the fluid-carrying channels of the cassette and with slits being provided in the matt channels that extend from the matt channels to a side of said matt facing the cassette such that said slits overlie said cassette fluid-carrying channels, said fluid-carrying channels being distinct from any pump and valve regions in said cassette, said slits extending longitudinally along at least part of a length of the matt channels so as to run substantially parallel therewith, said slits being repeatedly interrupted for short intervals to form slitted areas and non-slitted areas, said slits being configured to act as lip seals.

2. The device according to claim 1, wherein the matt channels in the slitted areas are more deeply recessed than in the non-slitted areas.

3. The device according to claim 1, wherein the elastic matt further includes connection channels having a shallower depth than a depth of said matt channels.

4. The device according to claim 3, wherein said connection channels extend to provide a continuous path around interruptions in the matt channels which correspond with machine-mounted pump membranes and valves.

5. The device according to claim 1, wherein the elastic matt is exchangeable.

6. The device according to claim 1, wherein the elastic matt is sealable around a perimeter area of the cassette by putting pressure onto a circumferential seal edge contained within the cassette area.

7. The device according to claim 1, wherein said cassette includes at least one of a valve region and a pump region, said matt further comprising a corresponding matt valve region or a corresponding matt pump region that overlies said valve and/or pump regions of said cassette, respectively.

8. The device according to claim 7, wherein said matt valve or pump region interrupts at least one of said matt channels to form two interrupted branches, said matt further including a connection channel that joins said two interrupted matt channel branches.

9. The matt according to claim 1, wherein said matt channels are elongated and substantially linear with a width of approximately 2 mm.

10. The device according to claim 1, wherein edge areas of said matt have the same substantially uniform thickness as non-recessed central areas of said matt.

11. The device according to claim 1, wherein the cassette-facing side of said matt is a flat surface, said flat surface extending uninterrupted over portions of said cassette-facing side positioned over said slitted areas.

12. A device for the treatment of a medical fluid, said device comprising a permanently installed fluid treatment machine and an elastic matt for attaching a cassette with fluid-carrying channels, said matt having a substantially uniform thickness into which channels are recessed, with a path of said matt channels being arranged to correspond with a path of fluid-carrying channels of a cassette to be attached, and slits being provided in the matt channels that extend from within the matt channels to an opposite side of said matt, said matt channels being distinct from any pump and valve regions in said matt, said matt further having a substantially rectangular shape that, when attached to a cassette, extends substantially across an entire face of the cassette to effect an even air exchange across said face and which can accommodate various arrangements of fixed components on the fluid treatment machine.

13. The device according to claim 12, wherein the elastic matt further includes connection channels having a shallower depth than a depth of said matt channels.

14. The device according to claim 12, wherein the slits extend longitudinally along at least part of a length of the matt channels so as to run substantially parallel therewith, said slits being repeatedly interrupted for short intervals to form slitted areas and non-slitted areas, said slits being configured to act as lip seals.

15. The device according to claim 14, wherein the matt channels in the slitted areas are more deeply recessed than in the non-slitted areas.

16. The device according to claim 12, wherein said matt channels are elongated and substantially linear with a width of approximately 2 mm.

17. The device according to claim 12, wherein edge areas of said matt have the same substantially uniform thickness as non-recessed central areas of said matt.

18. The device according to claim 12, wherein the opposite side of said matt is a flat surface, said flat surface extending uninterrupted over portions of said opposite side positioned over said slitted areas.

19. An elastic matt for use in a device for the treatment of a medical fluid, said device including a permanently installed fluid treatment machine and a cassette with fluid carrying channels and at least one of a valve region and a pump region distinct from said fluid carrying channels, said elastic matt comprising an exchangeable body member having a substantially rectangular shape that can accommodate various arrangements of fixed components on the fluid treatment machine and having a substantially uniform thickness into which a plurality of matt channels are recessed with paths of said matt channels respectively corresponding with paths of the fluid-carrying channels of the cassette and at least one of a matt valve region and a matt pump region distinct from said matt channels, said matt channels having a plurality of slits therein that extend from the matt channels to a side of said matt that faces the cassette, said elastic matt being placed between the fluid treatment machine and the cassette with said matt channels and slits in alignment with said cassette fluid-carrying channels and with said at least one matt valve region and said matt pump region in alignment with said at least one valve region and said pump region of said cassette, respectively.

20. The matt according to claim 19, wherein the elastic matt further includes connection channels having a shallower depth than a depth of said matt channels.

21. The matt according to claim 19, wherein the slits extend longitudinally along at least part of a length of the matt channels so as to run substantially parallel therewith, said slits being repeatedly interrupted for short intervals to form slitted areas and non-slitted areas.

22. The matt according to claim 21, wherein the matt channels in the slitted areas are more deeply recessed than in the non-slitted areas.

23. The matt according to claim 19, wherein said at least one valve region and pump region interrupts at least one matt channel to form two interrupted branches, said matt further including a connection channel that joins said two interrupted matt channel branches.

24. The matt according to claim 19, wherein edge areas of said matt body member have the same substantially uniform thickness as non-recessed central areas thereof.

25. A device for the treatment of a medical fluid, said device comprising a permanently installed fluid treatment machine, a cassette with fluid carrying channels and an elastic matt placed between the fluid treatment machine and the cassette, said elastic matt extending over substantially an entire face of said cassette and protecting an interior space of the fluid treatment machine, said matt having a substantially uniform thickness across said face into which channels are recessed, with paths of said matt channels respectively corresponding with paths of the fluid-carrying channels of the cassette and with slits being provided in the matt channels that extend from the matt channels to a side of said matt facing the cassette such that said slits overlie said cassette fluid-carrying channels, said fluid-carrying channels being distinct from any pump and valve regions in said cassette, said matt having a substantially rectangular shape that can accommodate various arrangements of fixed components on the fluid treatment machine.

26. The matt according to claim 19, wherein the cassette-facing side of said matt is a flat surface, said flat surface extending uninterrupted over portions of said cassette-facing side positioned over said slitted areas.

27. A device for the treatment of a medical fluid, said device comprising a permanently installed fluid treatment machine, a cassette with fluid carrying channels and an elastic matt placed between the fluid treatment machine and the cassette, said elastic matt extending over substantially an entire face of said cassette and protecting an interior space of the fluid treatment machine, said matt having a substantially uniform thickness across said face into which channels are recessed, with paths of said matt channels respectively corresponding with paths of the fluid-carrying channels of the cassette and with slits being provided in the matt channels that extend from the matt channels to a side of said matt facing the cassette such that said slits overlie said cassette fluid-carrying channels, said fluid-carrying channels being distinct from any pump and valve regions in said cassette, said elastic matt further including connection channels having a shallower depth than a depth of said matt channels, said connection channels extending to provide a continuous path around interruptions in the matt channels which correspond with machine-mounted pump membranes and valves.

* * * * *